US012702465B2

(12) United States Patent
Takei et al.

(10) Patent No.: US 12,702,465 B2
(45) Date of Patent: Aug. 11, 2026

(54) TREATMENT INSTRUMENT AND MANUFACTURING METHOD OF TREATMENT INSTRUMENT

(71) Applicant: OLYMPUS CORPORATION, Hachioji (JP)

(72) Inventors: Yusuke Takei, Hino (JP); Kazuhiro Tanaka, Hachioji (JP); Tomoyuki Takashino, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 10 days.

(21) Appl. No.: 18/243,253

(22) Filed: Sep. 7, 2023

(65) Prior Publication Data

US 2023/0414268 A1 Dec. 28, 2023

Related U.S. Application Data

(63) Continuation of application No. 16/878,998, filed on May 20, 2020, now Pat. No. 11,786,288, which is a (Continued)

(51) Int. Cl.
*A61B 18/08* (2006.01)
*A61B 18/00* (2006.01)
*A61B 18/14* (2006.01)

(52) U.S. Cl.
CPC ........ *A61B 18/085* (2013.01); *A61B 18/1442* (2013.01); *A61B 2018/00077* (2013.01); *A61B 2018/00702* (2013.01)

(58) Field of Classification Search
None
See application file for complete search history.

(56) References Cited

U.S. PATENT DOCUMENTS 5,169,397 A 12/1992 Sakashita et al.
2010/0204690 A1 8/2010 Bigley et al.
(Continued)

FOREIGN PATENT DOCUMENTS

CN 105979893 A 9/2016
CN 106456240 A 2/2017
(Continued)

OTHER PUBLICATIONS

Jan. 23, 2018 International Search Report issued in International Patent Application No. PCT/JP2017/042035.
(Continued)

*Primary Examiner* — Sean W Collins
*Assistant Examiner* — Nora W Rhodes
(74) *Attorney, Agent, or Firm* — Oliff PLC

(57) ABSTRACT

An electrically conductive plate of a treatment instrument includes a treating surface and a back surface facing an opposite side of the treating surface, and an electric component is arranged on the back surface of the electrically conductive plate. The electric component is electrically independent from the electrically conductive plate, and a holder supports the electrically conductive plate from the back surface side. A connector is made of a thermoplastic resin, and arranged on either side of and spaced from the electric component in a width direction intersecting with a longitudinal axis. The connector stationarily fixes each end of the electrically conductive plate in the width direction to the holder.

20 Claims, 12 Drawing Sheets

Related U.S. Application Data continuation of application No. PCT/JP2017/042035, filed on Nov. 22, 2017.

(56) References Cited

U.S. PATENT DOCUMENTS

| | | | | |
|---|---|---|---|---|
| 2013/0172887 | A1 | 7/2013 | Ichikawa et al. | |
| 2013/0226177 | A1 | 8/2013 | Brandt et al. | |
| 2014/0155877 | A1 | 6/2014 | Yasunaga | |
| 2016/0199124 | A1* | 7/2016 | Thomas | A61B 18/1445 606/41 |
| 2016/0310207 | A1 | 10/2016 | Honda et al. | |
| 2017/0042602 | A1 | 2/2017 | Takashino et al. | |
| 2017/0065325 | A1 | 3/2017 | Takei et al. | |
| 2017/0215941 | A1* | 8/2017 | Kazuno | A61B 18/1447 |
| 2017/0224406 | A1* | 8/2017 | Takei | A61B 18/10 |
| 2017/0238991 | A1* | 8/2017 | Worrell | H05K 1/034 |
| 2017/0245923 | A1* | 8/2017 | Takashino | A61B 18/085 |
| 2018/0125569 | A1 | 5/2018 | Vaders et al. | |
| 2018/0153613 | A1* | 6/2018 | Weisshaupt | A61B 18/1445 |

FOREIGN PATENT DOCUMENTS

| | | | | |
|---|---|---|---|---|
| JP | 2004-000460 | A | 1/2004 | |
| JP | 2005-177239 | A | 7/2005 | |
| JP | 2006-305236 | A | 11/2006 | |
| WO | WO-2015137139 | A1 * | 9/2015 | A61B 18/1445 |
| WO | 2016/067950 | A1 | 5/2016 | |
| WO | 2017/043120 | A1 | 3/2017 | |

OTHER PUBLICATIONS

Jun. 4, 2020 English Translation of the International Preliminary Report on Patentability issued in PCT Application No. PCT/JP2017/042035.

Nov. 3, 2022 Office Action issued in Chinese Patent Application No. 201780097070.5.

May 12, 2023 Office Action issued in Chinese Patent Application No. 201780097070.5.

* cited by examiner

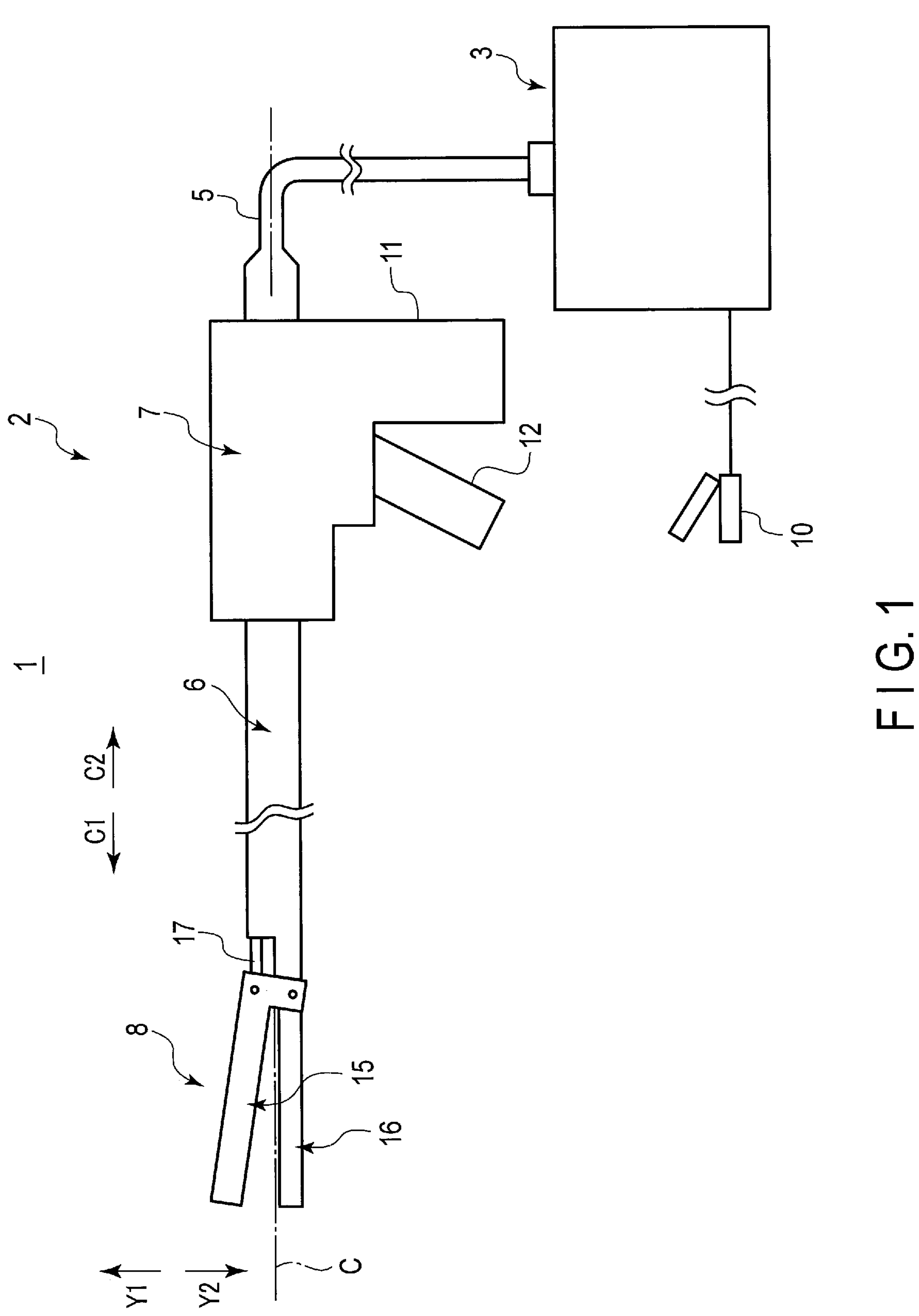
F I G. 1

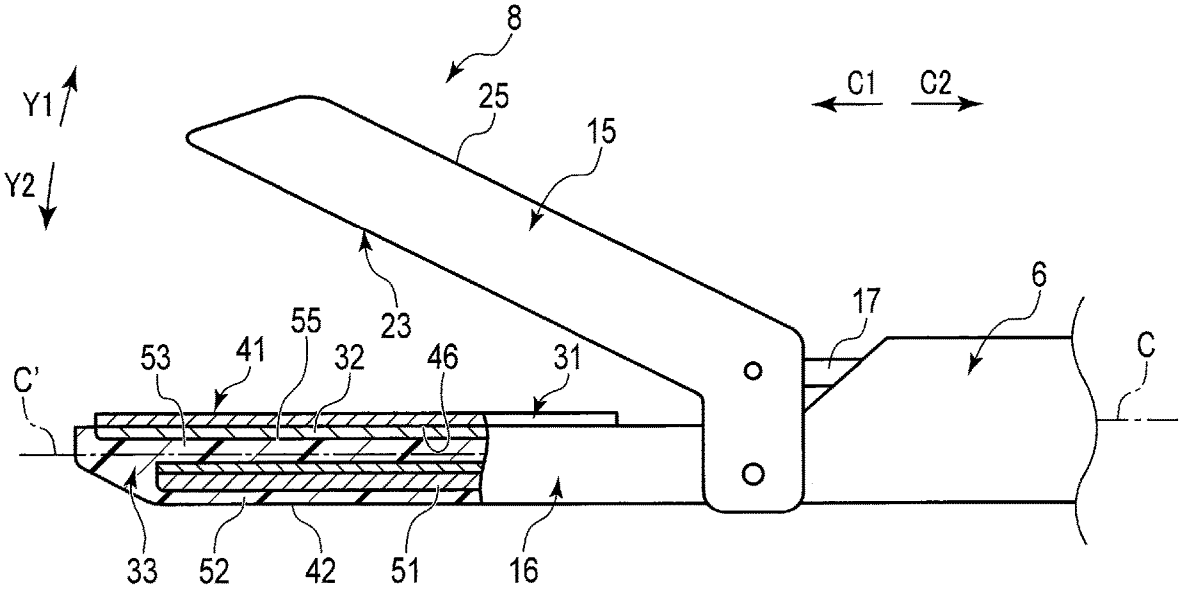
F I G. 2

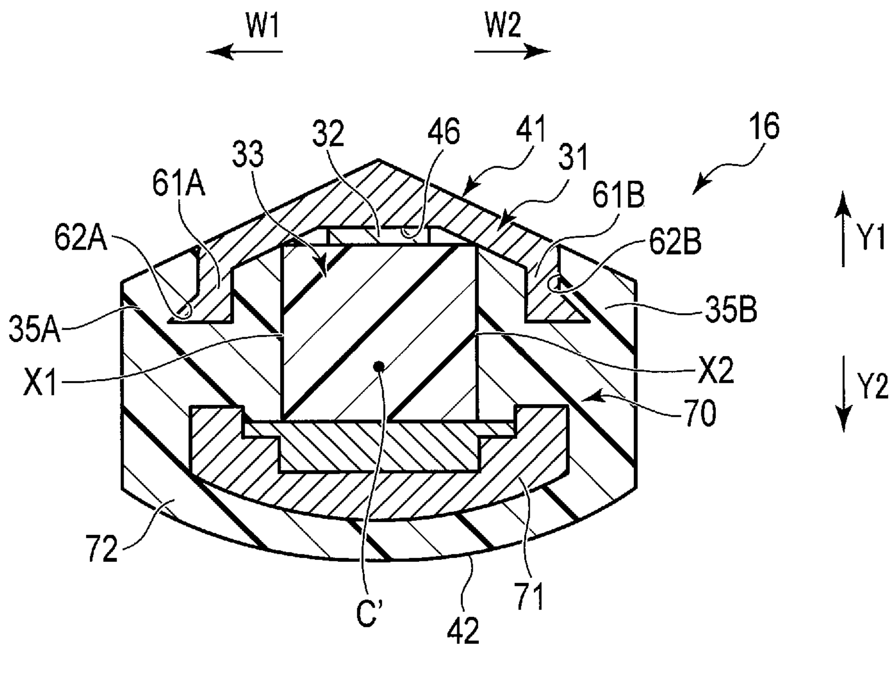
F I G. 5

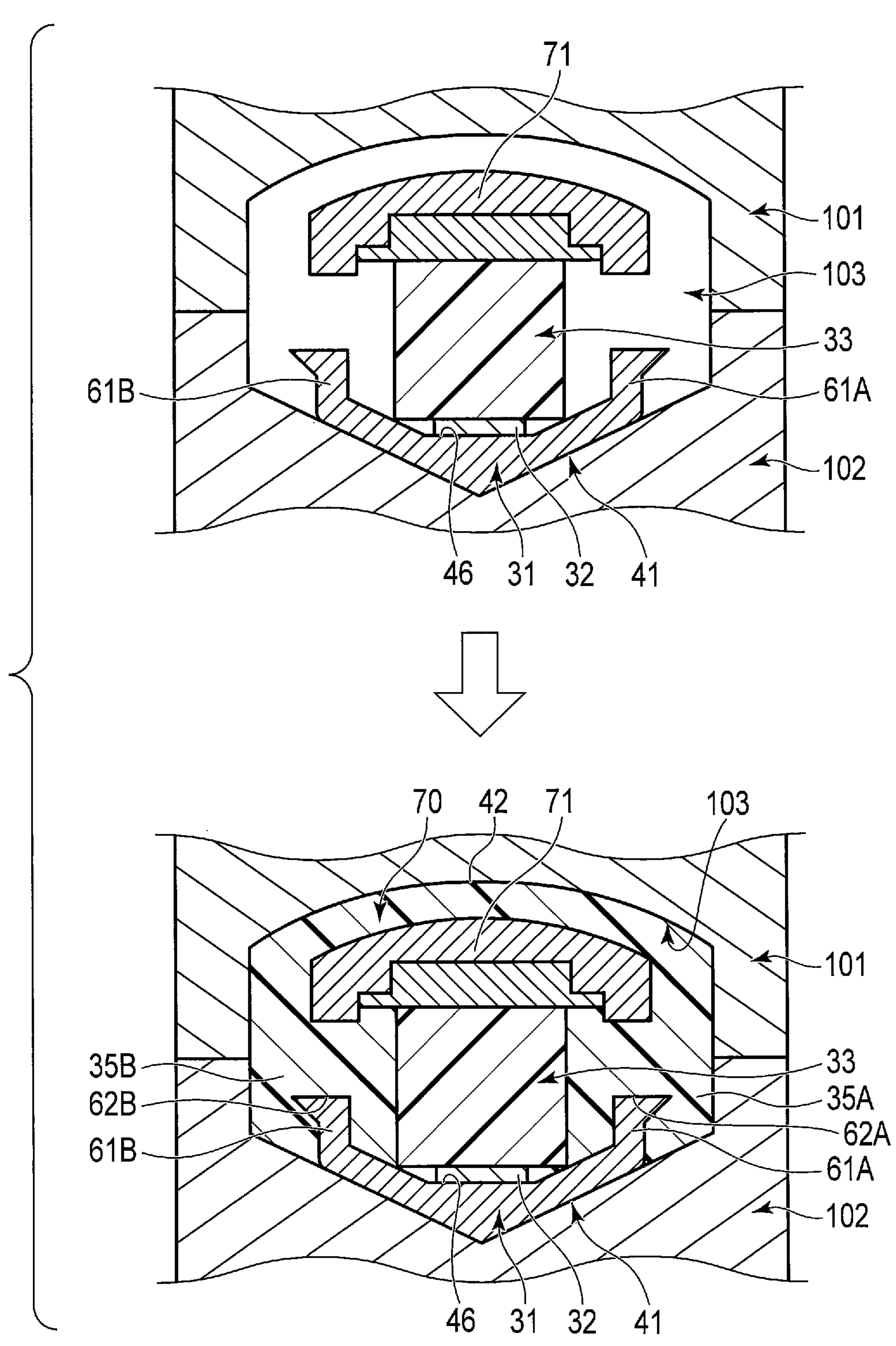
F I G. 6

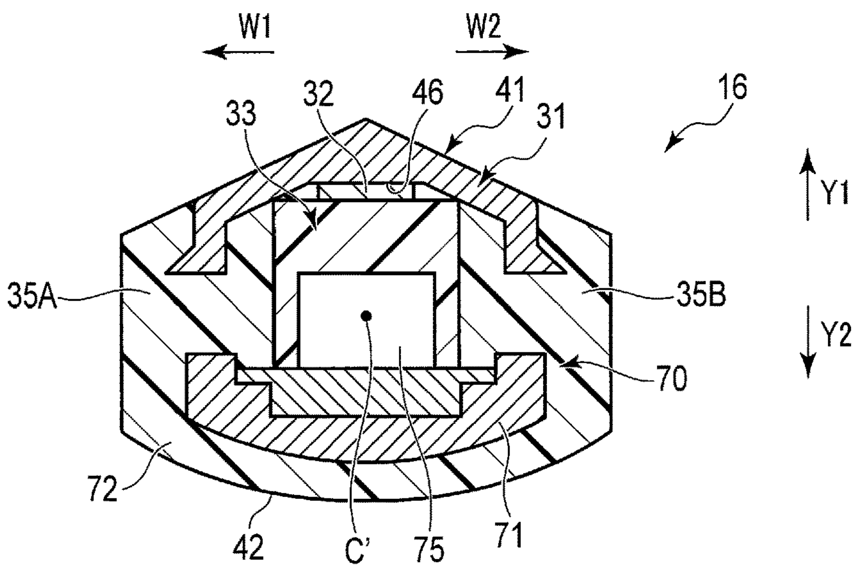
F I G. 7
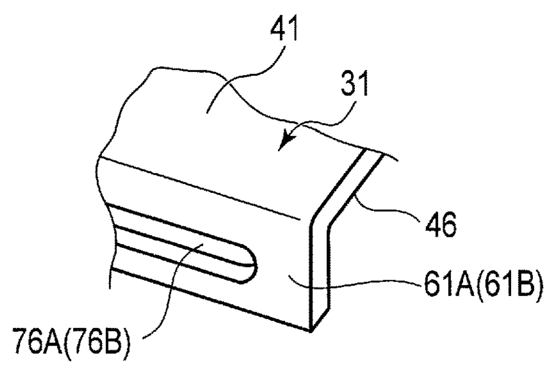
F I G. 8
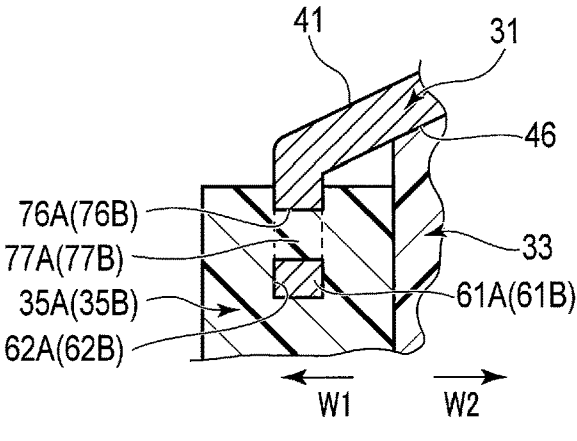
F I G. 9

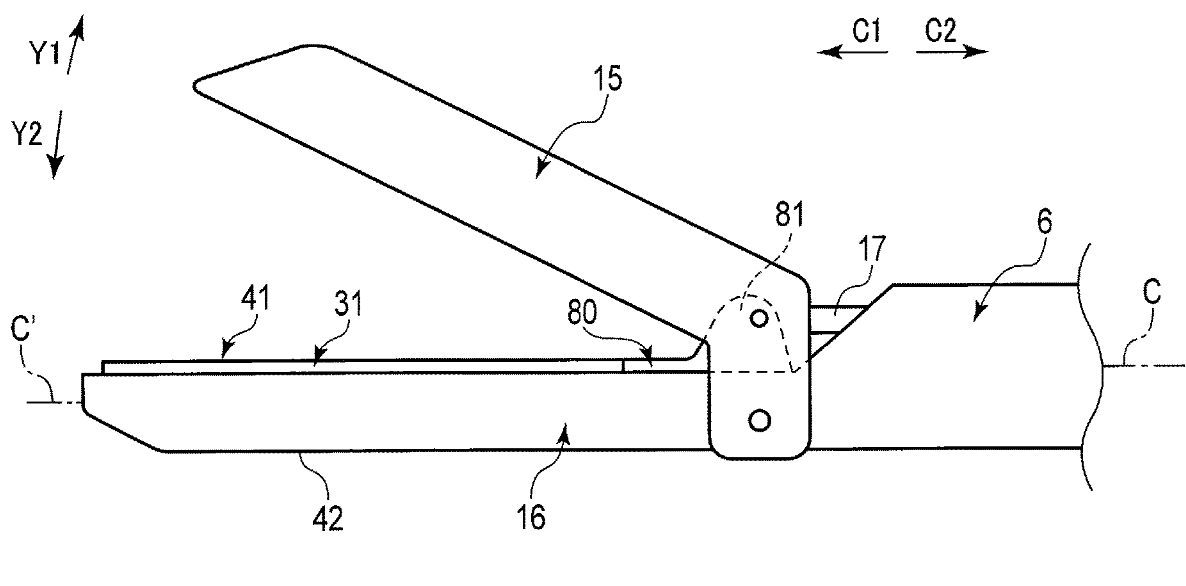
F I G. 10

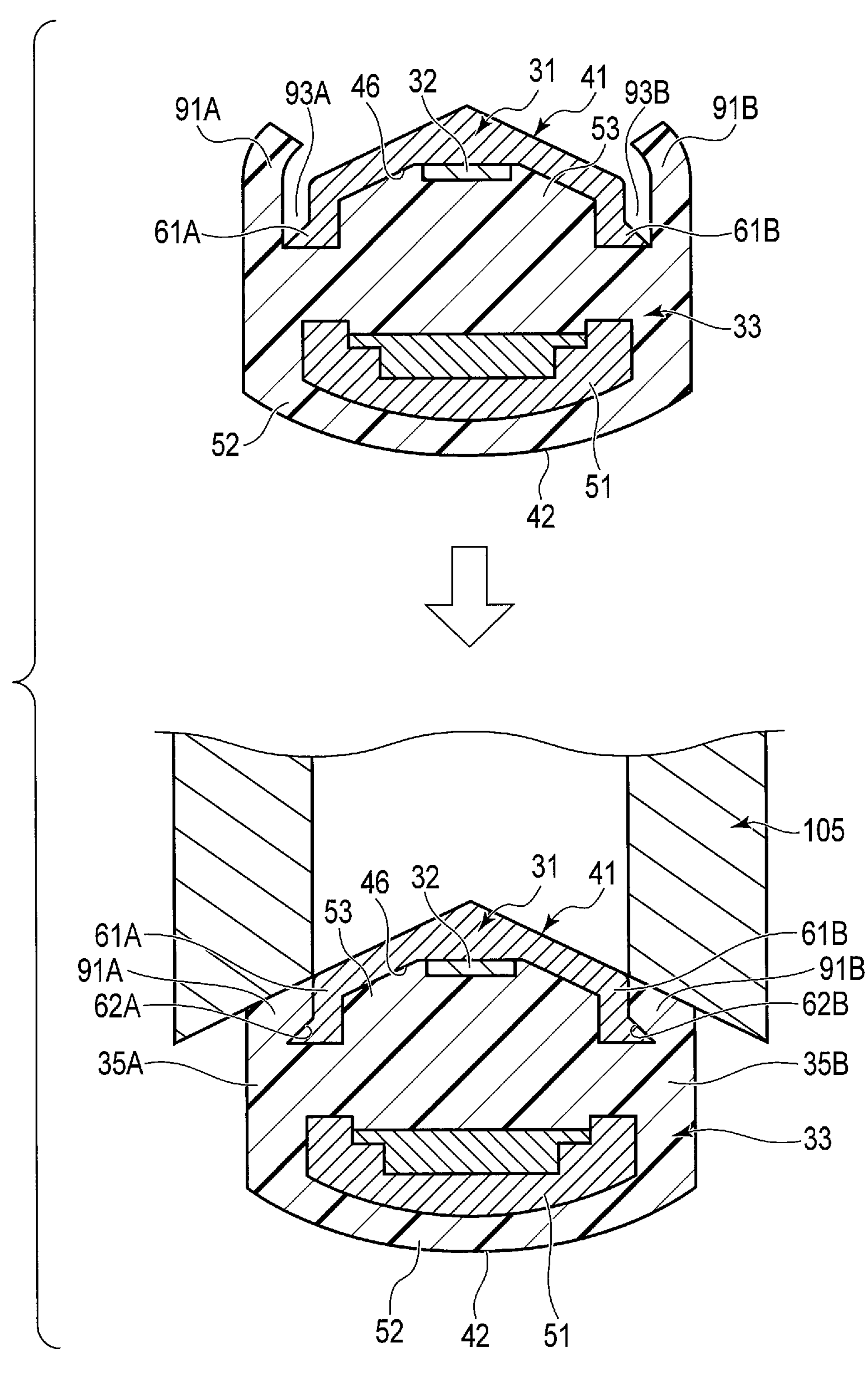
F I G. 14

TREATMENT INSTRUMENT AND MANUFACTURING METHOD OF TREATMENT INSTRUMENT

CROSS-REFERENCE TO RELATED APPLICATIONS

This is a Continuation application of U.S. application Ser. No. 16/878,998, filed May 20, 2020, which in turn is a Continuation application of PCT Application No. PCT/JP2017/042035, filed on Nov. 22, 2017. The disclosure of the prior applications is hereby incorporated by reference herein in its entirety.

BACKGROUND

1. Technical Field

The exemplary embodiments relate generally to a treatment instrument and a manufacturing method of the treatment instrument.

2. Description of the Related Art

A treatment instrument capable of grasping a treatment target between a pair of jaws (grasping pieces). In this treatment instrument, an electrically conductive plate (electrode) is provided in each of the jaws, and electric energy (high-frequency electric power) is supplied to each conductive plate, thereby allowing a high-frequency current to flow in the treatment target grasped between the electrically conductive plates.

SUMMARY

According to one aspect, a treatment instrument including: an electrically conductive plate including a treating surface configured to contact a treatment target, and a back surface facing an opposite side of the treating surface, the electrically conductive plate extending along a longitudinal axis; an electric component arranged on the back surface of the electrically conductive plate, the electric component being electrically independent from the electrically conductive plate; a holder supporting the electrically conductive plate and the electric component from a side of the back surface; and a connector made of a thermoplastic resin, the connector being arranged on either side of and spaced from the electric component in a width direction of the treatment instrument intersecting with the longitudinal axis, and the connector stationarily fixing each side end of the electrically conductive plate to the holder in the width direction.

According to one another aspect, a manufacturing method of a treatment instrument, the method including: forming an electrically conductive plate, the electrically conductive plate including a treating surface configured to contact a treatment target, and a back surface facing an opposite side of the treating surface, the electrically conductive plate extending along a longitudinal axis; arranging an electric component on the back surface of the electrically conductive plate, the electric component being electrically independent from the electrically conductive plate; forming a holder supporting the electrically conductive plate and the electric component from a side of the back surface; and softening or deforming a portion made of a thermoplastic resin in the holder by applying heat to the portion, or injecting a heated and softened thermoplastic resin, in a region distant from the electric component in width direction intersecting with the longitudinal axis, in a state in which the electrically conductive plate is supported by the holder; and cooling and hardening the deformed portion of the holder or the injected thermoplastic resin so as to stationarily fix each side end of the electrically conductive plate to the holder in the width direction.

Advantages of the exemplary embodiments will be set forth in the description which follows, and in part will be obvious from the description, or may be learned by practice of the exemplary embodiments. The advantages may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments, and together with the general description given above and the detailed description of the embodiments given below.

FIG. 1 is a schematic diagram of a treatment system of a first embodiment.

FIG. 2 is a schematic diagram of a distal portion of a shaft and an end effector of the first embodiment.

FIG. 5 is a cross-sectional view schematically showing either jaw according to a first modification of the first embodiment in a cross section perpendicular or substantially perpendicular to a longitudinal direction.

FIG. 6 is a schematic diagram explaining a process of forming connectors in manufacturing of either jaw according to the first modification of the first embodiment.

FIG. 7 is a cross-sectional view schematically showing either jaw according to a second modification of the first embodiment in a cross section perpendicular or substantially perpendicular to a longitudinal direction.

FIG. 8 is a schematic diagram showing an electrically conductive plate provided on either jaw according to a third modification of the first embodiment.

FIG. 9 is a cross-sectional view schematically showing a structure of a connector and its vicinity in either jaw according to a third modification of the first embodiment.

FIG. 10 is a schematic diagram showing a distal portion of a shaft and an end effector of a fourth modification of the first embodiment.

FIG. 14 is a schematic diagram explaining a process of forming connectors in manufacturing of either jaw in the second embodiment.

DETAILED DESCRIPTION

First Embodiment

Figure 3:
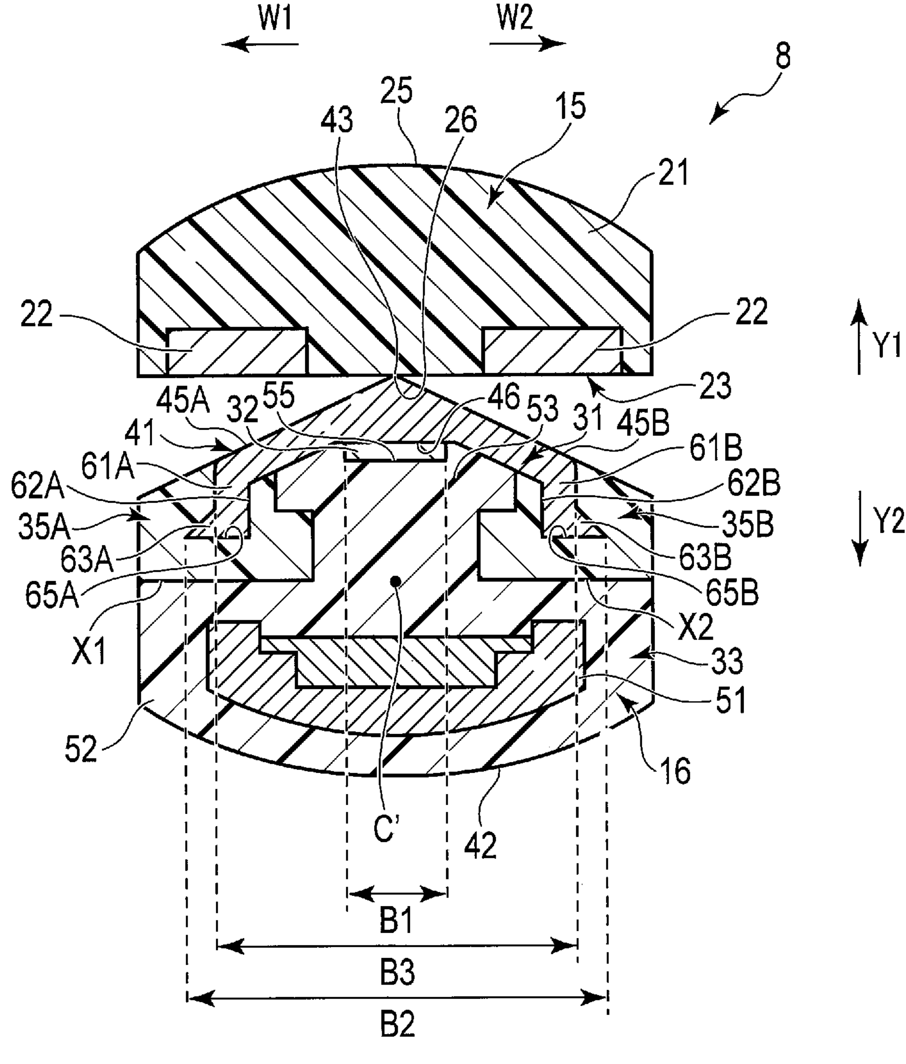
FIG. 3 is a cross-sectional view schematically showing the end effector of the first embodiment in a cross section perpendicular or substantially perpendicular to a longitudinal direction.

A first embodiment will be described with reference to FIGS. 1 to 4. FIG. 1 shows a treatment system 1 of the present embodiment. As shown in FIG. 1, the treatment system 1 includes a treatment instrument 2 and an electric power supply apparatus 3. The treatment instrument 2 is detachably connected to the electric power supply apparatus 3 via a cable 5. The treatment instrument 2 includes a cylindrical shaft (sheath) 6, a holdable housing 7, and an end effector 8. The shaft 6 has a longitudinal axis C as a center axis. Herein, one side along the longitudinal axis C is defined as a distal side (arrow C1 side), and a side opposite to the distal side is defined as a proximal side (arrow C2 side). The shaft 6 extends along the longitudinal axis C from the proximal side to the distal side, and the housing 7 is coupled to the proximal side of the shaft 6. The end effector 8 is connected to the distal side of the shaft 6, and extends from the distal portion of the shaft 6 toward the distal side. The end effector 8 extends along the longitudinal direction of the end effector 8, from the proximal portion toward the distal portion.

The housing 7 includes a grip 11 that extends in a direction intersecting with the longitudinal axis C. To this housing 7, a handle 12 is pivotably attached. When the handle 12 pivots relative to the housing 7, the handle 12 opens or closes with respect to the grip 11. In the present embodiment, one end of the cable 5 is connected to the housing 7. The other end of the cable 5 is detachably connected to the electric power supply apparatus 3. An operation apparatus 10, such as a foot switch, is electrically connected to the electric power supply apparatus 3. In the operation apparatus 10, an operation to cause the electric power supply apparatus 3 to output electric energy to the treatment instrument 2 is input. In one example, instead of or in addition to the operation apparatus 10 provided separately from the treatment instrument 2, an operating button, etc. attached to the housing 7, etc. of the treatment instrument 2 is provided as an operation apparatus. With this operation apparatus attached to the treatment instrument 2, an operation to cause the electric power supply apparatus 3 to output electric energy to the treatment instrument 2 is input.

FIG. 2 shows configurations of the distal portion of the shaft 6 and the end effector 8. As shown in FIGS. 1 and 2, the end effector 8 includes a pair of jaws (grasping pieces) 15 and 16. Each of the jaws 15 and 16 continuously extends from the proximal portion to the distal portion of the end effector 8, along the longitudinal direction of the end effector 8. The jaws 15 and 16 as a pair can close and open with respect to each other. In one example, one of the jaws 15 and 16 is integrated into the shaft 6 or stationarily fixed to the shaft 6, and the other of the jaws 15 and 16 is pivotably attached to the shaft 6. In another example, both of the jaws 15 and 16 are pivotably attached to the shaft 6. The opening and closing directions (the directions indicated by arrows Y1 and Y2) of the end effector 8, in other words, the moving directions of the jaws 15 and 16 in the opening and closing movements of the end effector 8, intersect with (are perpendicular or substantially perpendicular to) the longitudinal direction of the end effector 8.

In the inside of the housing 7, the proximal portion of a movable member 17 is coupled to the handle 12. The movable member 17 is movable along the longitudinal axis C relative to the shaft 6 and the housing 7. The distal end of the movable member 17 is coupled to at least one of the jaws 15 and 16. By opening or closing the handle 12 with respect to the grip 11, the movable member 17 moves along the longitudinal axis C. Thus, at least one of the jaws 15 and 16 pivots, and the jaws 15 and 16 open or close with respect to each other. When they are closed with respect to each other, it is thus possible to grasp a treatment target, such as living tissue, between the jaws 15 and 16. In one example, an operation member, such as a rotative knob, etc., is attached to the housing 7. When an operation is input at the operation member, the end effector 8 and the shaft 6 together rotate around the longitudinal axis C relative to the housing 7.

In another example, an operation member, such as a dial, is provided in the housing 7, and the end effector 8 bends or curves with respect to the shaft 6 and the longitudinal axis C in response to an operation input at the operation member. In this example, a relaying member (not shown) provided in the end effector 8 is attached to the shaft 6 in a bendable or curvable manner. One of the jaws 15 and 16 is pivotably attached to the relaying member. The other of the jaws 15 and 16 may be integrated into, stationarily fixed to, or pivotably attached to the relaying member.

FIG. 3 shows the end effector 8 in a cross section perpendicular or substantially perpendicular to the longitudinal direction (a cross section intersecting with the longitudinal direction). FIG. 3 shows a state where the jaws 15 and 16 are closed with respect to each other.

Herein, in the end effector 8, suppose the direction intersecting with (perpendicular or substantially perpendicular to) the longitudinal direction, and intersecting with (perpendicular or substantially perpendicular to) the opening and closing directions of the end effector 8 (the directions indicated by arrows Y1 and Y2) is "width direction" (the direction indicated by arrows W1 and W2). In one example, in each of the jaws 15 and 16, the dimension in the longitudinal direction is greater than the dimension in the width direction. As shown in FIGS. 2 and 3, in the present embodiment, the jaw 15 includes a holder 21 and an electrically conductive plate (electrode) 22. Each of the holder 21 and the electrically conductive plate 22 continuously extends from the proximal portion to the distal portion of the jaw 15, in the longitudinal direction of the end effector 8. The holder 21 is made of a resin, etc., having thermal resistance and electric insulation properties, for example. In one example, the holder 21 may be made by insert molding, etc. so as to encapsulate a core made of a metal, etc. with a resin. The electrically conductive plate 22 is made of a metal, etc. having electrical conductivity.

The jaw 15 includes a grasping surface (opposing surface) 23 opposing to the other jaw 16, and a back surface 25 facing the opposite side of the grasping surface 23. Each of the grasping surface 23 and the back surface 25 continuously extends from the proximal portion to the distal portion of the jaw 15, along the longitudinal direction of the end effector 8. In the present embodiment, the holder 21 and the electrically conductive plate 22 constitute the grasping surface 23, and the holder 21 constitutes the back surface 25. In a state in which a treatment target is grasped between the jaws 15 and 16, the treatment target is in contact with the grasping surface 23. On the grasping surface 23, an abutting portion 26 to which the jaw 16 can abut while the jaws 15 and 16 are closed with respect to each other is provided. The abutting portion 26 is formed by the holder 21, and is made of a material having electric insulation properties. In the present embodiment, the abutting portion 26 continuously extends from the proximal portion to the distal portion of the jaw 15, in the longitudinal direction of the end effector 8, and is formed in the center of the jaw 15 according to the width direction of the end effector 8. On the grasping surface 23, the electrically conductive plates 22 are provided on both sides of the abutting portion 26 in the width direction of the end effector 8.

In a not-shown example, the holder 21 has a frame made of a metal, etc. and having appropriate rigidity, and this frame constitutes the back surface 25. When the frame has electrical conductivity, the outer peripheral surface of the frame is entirely coated with a material having electric insulation properties, such as polytetrafluoroethylene (PTFE).

The other jaw 16 has a longitudinal axis C' as a center axis, and extends along the longitudinal axis C', from its proximal end to its distal end. When the jaws 15 and 16 are closed with respect to each other, the longitudinal axis C' of the jaw 16 is parallel or substantially parallel to the longitudinal direction of the end effector 8. The opening and closing directions of the end effector 8 intersect with (are perpendicular or substantially perpendicular to) the longitudinal axis C'. Furthermore, the width direction of the end effector 8 intersect with (are perpendicular or substantially perpendicular to) the longitudinal axis C', and intersect with (are perpendicular or substantially perpendicular to) the opening and closing directions of the end effector 8. The jaw 16 includes an electrically conductive plate (blade) 31, a heater 32 which is an electric component, a holder 33, and connectors 35A and 35B. Each of the electrically conductive plate 31, the heater 32, the holder 33, and the connectors 35A and 35B continuously extends from the proximal portion to the distal portion of the jaw 16, in a direction along the longitudinal direction C' (the longitudinal direction of the end effector 8).

The jaw 16 includes a treating surface (opposing surface) 41 opposing to the grasping surface 23, and a back surface 42 facing the opposite side of the treating surface 41. Each of the treating surface (grasping surface) 41 and the back surface 42 continuously extends from the proximal portion to the distal portion of the jaw 16, in the direction along the longitudinal axis C' (the longitudinal direction of the end effector 8). In the present embodiment, the electrically conductive plate 31 constitutes the treating surface 41, and the holder 33 constitutes the back surface 42. For this reason, in the present embodiment, the jaw 15 is arranged in such a manner that it faces the treating surface 41 of the electrically conductive plate 31, and the space between the electrically conductive plate 31 and the jaw 15 can be open or closed. In a state in which a treatment target is grasped between the jaws 15 and 16, the treatment target is in contact with the treating surface 41.

The electrically conductive plate 31 is made of a metal, etc. having electrical conductivity; in the present embodiment, the electrically conductive plate 31 is made of a material having properties of high thermal conductivity (a high thermal conductivity rate). In the electrically conductive plate 31, a projection 43 that projects toward the jaw 15 side is formed. At the projection 43, the treating surface 41 projects toward the jaw 15 side, compared to the portions other than the projection 43. In the present embodiment, the projection 43 continuously extends from the proximal portion to the distal portion of the jaw 16 (the electrically conductive plate 31) in the direction along the longitudinal axis C', and is formed in the center of the jaw 16 according to the width direction of the end effector 8. In the treating surface 41, the inclined surfaces 45A and 45B are formed on respective sides of the projection 43 in the width direction of the end effector 8. The inclined surfaces 45A and 45B are formed by the electrically conductive plate 31, and continuously extend from the proximal portion to the distal portion of the jaw 16 (the electrically conductive plate 31) in the direction along the longitudinal axis C'. Each of the inclined surfaces 45A and 45B is inclined in a state that the surface extends toward the side on which the jaw 16 opens as the surface becomes distant from the projection 43 in the width direction. The projection 43 may be formed with an acute or obtuse angle.

In a state where the jaws 15 and 16 are closed to each other, the projection 43 of the electrically conductive plate 31 is abutted to the abutting portion 26 of the jaw 15. However, even when the electrically conductive plate 31 is abutted to the abutting portion 26, the electrically conductive plate 31 is located at a distance from the electrically conductive plate 22 of the jaw 15 and does not come into contact with the electrically conductive plate 22. For this reason, the contact between the electrically conductive plates 22 and 31 can be effectively prevented.

The electrically conductive plate 31 includes a back surface (plate back surface) 46 facing the opposite side of the treating surface 41. The back surface 46 faces the side on which the jaw 16 opens. The heater 32 is provided on the back surface 46, and is stationarily fixed to the electrically conductive plate 31 on the back surface 46. In the present embodiment, the heater 32 is provided in the center of the jaw 16 in the width direction of the end effector 8. The dimension B1 of the heater 32 in the width direction of the end effector 8 is smaller than the dimension B2 of the electrically conductive plate 31 in the width direction of the end effector 8. Furthermore, the dimension B1 is smaller than the dimension B3 of the treating surface 41 in the width direction of the end effector 8. The heater 32 is electrically insulated from the electrically conductive plate 31 by an insulating layer (not shown). For this reason, the heater 32 which is an electric component is electrically independent from the electrically conductive plate 31.

In the present embodiment, upon an input of an operation at the operation apparatus 10, high-frequency electric power is output from the electric power supply apparatus 3 to the electrically conductive plates 22 and 31 as electric energy. Thus, the electrically conductive plates 22 and 31 function as electrodes having electric potentials differing from each other. In a state in which a treatment target is grasped between the jaws 15 and 16, when electric energy is supplied to the electrically conductive plates 22 and 31, a high-frequency current flows between the electrically conductive plates 22 and 31 via the grasped treatment target, and the high-frequency current is thereby applied to the treatment target.

In the present embodiment, when an operation is input at the operation apparatus 10, direct current electric power or alternating current electric power is output from the electric power supply apparatus 3 to the heater 32. At this time, the electric energy is supplied to the heater 32 through an electric path which is independent from an electric path for supplying electric energy to the electrically conductive plates 22 and 31. When the electric energy is supplied to the heater 32, the electric energy is converted into thermal energy due to electric resistance of the heater 32, and heat is thereby generated. The heat generated in the heater 32 is transferred to the treating surface 41 via the electrically conductive plate 31. In a state in which the treatment target is grasped between the jaws 15 and 16, when the electric energy is supplied to the heater 32, the heat generated by the heater 32 is applied to the treatment target from the treating surface 41.

The holder 33 supports the electrically conductive plate 31 from the back surface 46 side, namely, the side on which the jaw 16 opens. In the present embodiment, the holder 33 includes a core member 51 made of a metal, etc., and a coating 52 that coats the core member 51. Each of the core member 51 and the coating 52 continuously extends from the proximal portion tow the distal portion of the jaw 16 (holder 33) in a direction along the longitudinal axis C'. The coating 52 is made of a material having thermal resistance and electric insulation properties, and properties of low thermal conductivity (a low thermal conductivity rate). Accordingly, the coating 52 of the holder 33 has lower thermal conductivity than that of the electrically conductive plate 31. The coating 52 is formed by insert molding (injection molding) wherein a resin is inserted into the core member 51, for example. In one example, the coating 52 is formed by a resin with glass bubbles added to it. In another example, a foaming resin, in other words, a porous resin, forms the coating 52.

The coating 52 includes a supporting projection 53 projecting toward the electrically conductive plate 31, namely the side on which the jaw 16 closes. In the present embodiment, the supporting projection 53 continuously extends from the proximal portion to the distal portion of the jaw 16 (holder 33), in the longitudinal direction of the end effector 8, and is formed in the center of the jaw 16 according to the width direction of the end effector 8. The electrically conductive plate 31 is supported by the supporting projection 53 from the back surface 46 side, and the supporting projection 53 is abutted to the back surface 46 of the electrically conductive plate 31.

On the projection end surface of the supporting projection 53, a mating concave portion 55 is formed in such a manner that its concave portion is concaved toward the side on which the jaw 16 opens. In the present embodiment, the mating concave portion 55 continuously extends from the proximal portion to the distal portion of the jaw 16 (holder 33), in the longitudinal direction of the end effector 8, and is formed in the center of the supporting projection 53 according to the width direction of the end effector 8. The heater 32 stationarily fixed to the back surface 46 of the electrically conductive plate 31 fits into the mating concave portion 55, and engages the mating concave portion 55. For this reason, in the jaw 16, the heater 32 is arranged between the electrically conductive plate 31 and the holder 33 in the opening and closing directions of the end effector 8. Since the coating 52 of the holder 33 is made of a material having low thermal conductivity as described above, transfer of the heat generated in the heater 32 and Joule heat caused by a high-frequency current to the back surface 42 of the jaw 16 is difficult. For this reason, the increase of a temperature of the back surface 42 in the jaw 16 due to the heat of the heater 32 and the Joule heat caused by the high-frequency current can be effectively prevented.

In the jaw 16, a connector (first connector) 35A is provided on one side relative to the supporting projection 53 of the holder 33 in the width direction, and a connector (second connector) 35B is provided on the other side relative to the supporting projection 53 in the width direction. For this reason, the supporting projection 53 is interposed between the connectors 35A and 35B according to the width direction, and the connector 35A is provided on the opposite side of the connector 35B with respect to the longitudinal axis C' in the width direction. Each of the connectors 35A and 35B is arranged at a distance from the heater 32 toward an outer side in the width direction of the end effector 8, and is stationarily fixed to the holder 33. One end of the electrically conductive plate 31 in the width direction is stationarily fixed to the holder 33 by the connector 35A. And the other end of the electrically conductive plate 31 in the width direction is stationarily fixed to the holder 33 by the connector 35B. In other words, each of the connectors 35A and 35B stationarily fixes a corresponding one of the ends of the electrically conductive plate 31 in the width direction to the holder 33.

Each of the connectors 35A and 35B is made of a thermoplastic resin. The thermoplastic resin that constitutes each of the connectors 35A and 35B has thermal resistance and electric insulation properties, and has properties of low thermal conductivity (a low thermal conductivity rate). For this reason, each of the connectors 35A and 35B has lower heat thermal conductivity than that of the electrically conductive plate 31. Examples of the thermoplastic resin constituting each of the connectors 35A and 35B are: liquid crystal polymer (LCP), polyetheretherketone (PEEK), perfluoroalkoxy alkane (PFA), polytetrafluoroethylene (PTFE), polyimide (PI), and polybenzimidazole (PBI), and the like. The resin constituting the coating 52 of the holder 33 may have the same composition as the resin constituting the connectors 35A and 35B, or a composition differing from the resin constituting the connectors 35A and 35B. However, it is preferable that the coating 52 of the holder 33 be made of a resin having the same composition as the resin constituting the connectors 35A and 35B.

In the present embodiment, each of the connectors 35A and 35B is a member separate from the coating 52 of the holder 33. For this reason, in the jaw 16, an interface X1 is formed between the connector 35A and the coating 52, and an interface X2 is formed between the connector 35B and the coating 52. Each of the interfaces X1 and X2 continuously extends from the proximal portion to the distal portion of the jaw 16, in the direction along the longitudinal axis C' (the longitudinal direction of the end effector 8).

The thermoplastic resin constituting the connectors 35A and 35B has a melting point higher than a temperature of the treating surface 41 when treatment energy, such as the heat generated at the heater 32 or a high-frequency current, is applied to the treatment target. Herein, in a state where the treatment target is undergoing dissection using the heat generated in the heater 32, the temperatures of the heater 32 and the treating surface 41 are, for example, around 300° C. For this reason, in the treatment instrument 2 that conducts dissection (cutting) of the treatment target using the heat generated by the heater 32, the connectors 35A and 35B are made of a thermoplastic resin that has a melting point higher than 300° C. and that does not become softened to a deformable extent at the temperature of 300° C. and the vicinity thereof. From this point of view, in the treatment instrument 2 that conducts dissection of the treatment target using the heat generated by the heater 32, LCP or PEEK, for example, is selected as a thermoplastic resin for constituting the connectors 35A and 35B. The resin that constitutes the coating 52 of the holder 33 also has a melting point higher than the temperature of the treating surface 41 when treatment energy is applied to the treatment target. For this reason, the resin that forms the coating 52 does not become softened to a deformable extent at the temperature of 300° C. or the vicinity thereof.

In the electrically conductive plate 31, an engagement claw 61A is provided in one end according to the width direction, and an engagement claw 61B is provided in the other end according to the width direction. The engagement claw 61A is arranged on the opposite side of the engagement claw 61B with respect to the longitudinal axis C' in the width direction. Each of the engagement claws 61A and 61B is formed continuously over the entire or substantially entire length of the electrically conductive plate 31 in the direction along the longitudinal axis C', and projects toward the side on which the jaw 16 opens in the electrically conductive plate 31. An engagement groove 62A which the engagement claw 61A engages is formed in the connector 35A, and an engagement groove 62B which the engagement claw 61B engages is formed in the connector 35B. Each of the engagement grooves 62A and 62B continuously extends from the proximal portion to the distal portion of the jaw 16, in the direction along the longitudinal axis C'. In the connector 35A, the engagement groove 62A is recessed toward the side on which the jaw 16 opens, and in the connector 35B, the engagement groove 62B is recessed toward the side on which the jaw 16 opens.

In the cross section perpendicular or substantially perpendicular to the longitudinal axis C' (the cross section intersecting with the longitudinal axis C'), the cross-sectional shape of each of the engagement grooves 62A and 62B is the same as the cross-sectional shape of a corresponding one of the engagement claws 61A and 61B. For this reason, in the engagement groove 62A, a pressing pressure, etc. applied to the engagement claw 61A from the connector 35A can prevent an escape of the engagement claw 61A from the engagement groove 62A, and a release of the engagement between the engagement claw 61A and the engagement groove 62A. Similarly, in the engagement groove 62B, a pressing pressure, etc. applied to the engagement claw 61B from the connector 35B can prevent an escape of the engagement claw 61B from the engagement groove 62B, and a release of the engagement between the engagement claw 61B and the engagement groove 62B. Accordingly, in the present embodiment, one end of the electrically conductive plate 31 in the width direction is firmly fixed to the holder 33 by the engagement between the engagement claw 61A and the engagement groove 62A, and the other end of the electrically conductive plate 31 in the width direction is firmly fixed to the holder 33 by the engagement between the engagement claw 61B and the engagement groove 62B.

The projection end and the vicinity thereof in each of the engagement claws 61A and 61B forms an anchor shape (either one of 63A or 63B) that becomes acute (radical) toward the outward side in the width direction in the cross section perpendicular or substantially perpendicular to the longitudinal axis C'. Furthermore, in the cross section perpendicular or substantially perpendicular to the longitudinal axis C', the cross-sectional shape of the bottom and its vicinity of each of the engagement grooves 62A and 62B is the same anchor shape (either one of 65A or as the anchor shape (either one of 63A or 63B) of the engagement claw (either one of 61A or 61B) that engages the groove. For this reason, an escape of the engagement claw (either one of 61A or 61B) from the corresponding engagement groove (either one of 62A or 62B) can be effectively prevented, and a coupling strength of a corresponding connector (either one of 35A or 35B) of the engagement claw 61A or 61B can be improved. The electrically conductive plate 31 is thereby firmly coupled to the holder 33.

In one example, each of the engagement claws 61A and 61B is formed discontinuously in the direction along the longitudinal axis C'. In this case, each of the engagement grooves 62A and 62B is formed discontinuously in the direction along the longitudinal axis C' in correspondence to the engagement claws 61A and 61B. Furthermore, the corresponding one of the engagement claws 61A and 61B engages each of the engagement grooves 62A and 62B.

Next, a method of manufacturing the treatment instrument 2, particularly a method of manufacturing the jaw 16 in which the heater 32 is provided as an electric component, will be described. When the jaw 16 is formed, the electrically conductive plate 31 including the treating surface 41, the back surface 46, and the engagement claws 61A and 61B, is made from a material having electrical conductivity such as a metal. Furthermore, the heater 32 which is an electric component is arranged on the back surface 46 of the electrically conductive plate 31, and stationarily fixed to the electrically conductive plate 31. At this time, the heater 32 is arranged in a manner such that the heater 32 is electrically independent from the electrically conductive plate 31, through provision of an electrically insulating layer, etc. between the back surface 46 of the electrically conductive plate 31 and the heater 32. In the manufacturing of the jaw 16, the holder 33 is formed. When the holder 33 is formed, the coating 52 is formed by insert molding (injection molding) of a resin into the core member 51, for example. Then, the electrically conductive plate 31 in which the heater 32 is stationarily fixed to the back surface 46 is supported by the holder 33 from the back surface 46 side. At this time, the supporting projection 53 of the holder 33 is abutted to the back surface 46 of the electrically conductive plate 31, and the heater 32 fits into the mating concave portion 55 of the holder 33. Then, the heater 32 is arranged between the electrically conductive plate 31 and the holder 33.

Figure 4:
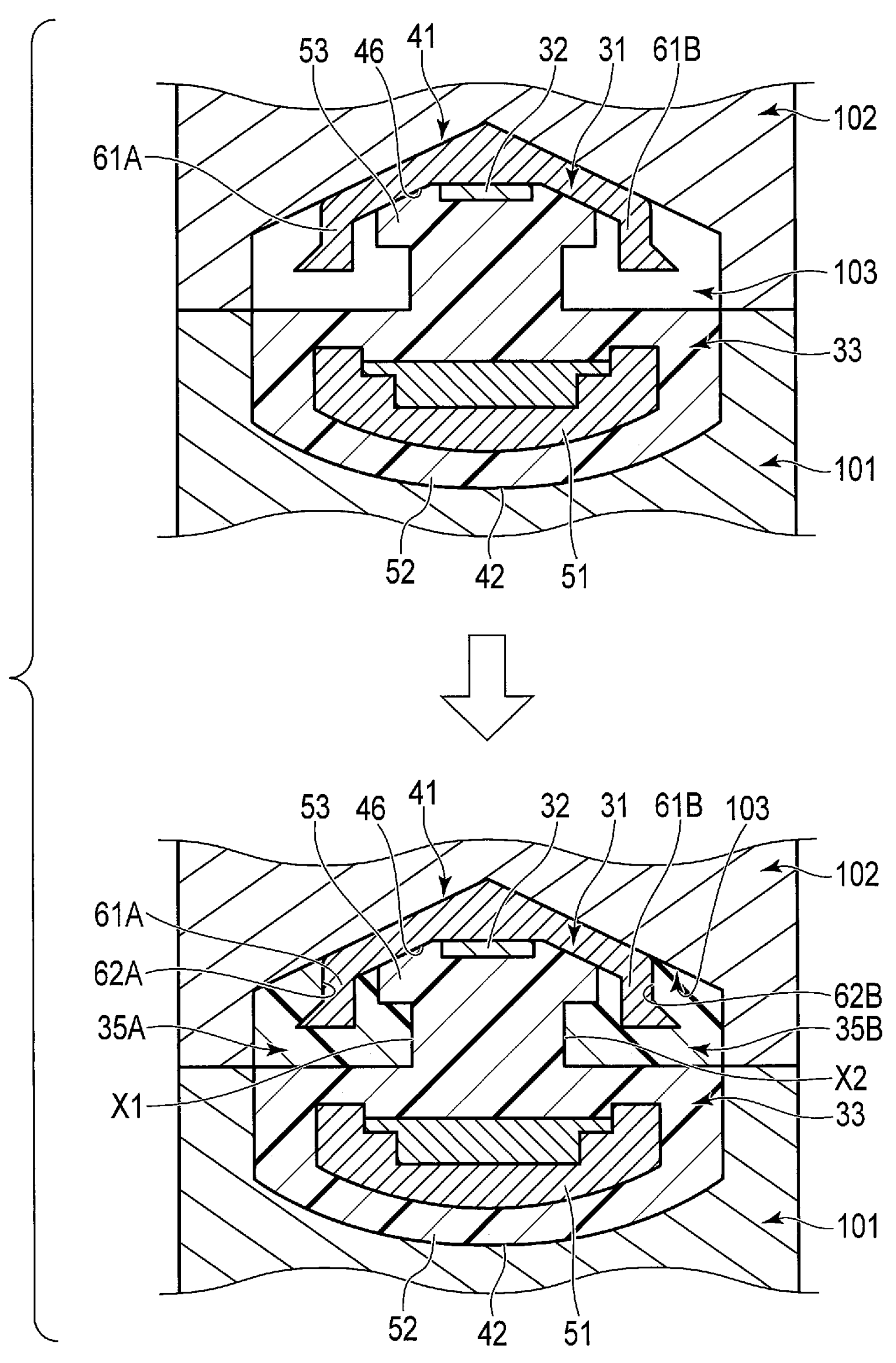
FIG. 4 is a schematic diagram explaining a process of forming connectors in manufacturing of either jaw in the first embodiment.

FIG. 4 shows the process of forming the connectors 35A and 35B. As shown in FIG. 4, the connectors 35A and 35B are formed using a pair of dies 101 and 102 capable of opening and closing with respect to each other. Herein, one die 101 is a fixed type and the other die 102 is a movable type, as an example. If the dies 101 and 102 are closed to each other, a cavity 103 is generated between the dies 101 and 102. When the connectors 35A and 35B are formed, the electrically conductive plate 31, the heater 32, and the holder 33 are stationarily fixed to the die 101, with the dies 101 and 102 being open to each other. At this time, with the electrically conductive plate 31 being supported by the holder 33 from the back surface 46 side, the electrically conductive plate 31, the heater 32, and the holder 33 are arranged.

Then, the dies 101 and 102 are closed to each other, and the electrically conductive plate 31, the heater 32, and the holder 33 are arranged in the cavity 103 thereby formed. At this time, in the cavity 103, a space is formed in each area on both sides of the supporting projection 53 of the holder 33 in the width direction of the jaw 16. In the space formed in the cavity 103, the engagement claw 61A is arranged on one side relative to the holder 33 in the width direction, and the engagement claw 61B is arranged on the other side relative to the holder 33 in the width direction. In the cavity 103, a heated and softened thermoplastic resin is injected into the space on both sides relative to the supporting projection 53 in the width direction. In other words, the thermoplastic resin is injected into a region distant from the heater 32 in the width direction. Then, the injected thermoplastic resin is cooled and hardened. At this time, the thermoplastic resin is naturally cooled, for example. Thus, the thermoplastic resin forms into the connectors 35A and 35B on both sides of the supporting projection 53 in the width direction. In other words, the connectors 35A and 35B are formed using the thermoplastic resin by insert molding at a region distant from the heater 32 in the width direction.

Through the formation of the connector 35A, one end of the electrically conductive plate 31 in the width direction is stationarily fixed to the holder 33. And through the formation of the connector 35B, the other end of the electrically conductive plate 31 in the width direction is stationarily fixed to the holder 33. The interface X1 is formed between the connector 35A and the holder 33 by forming the connector 35A, and the interface X2 is formed between the connector 35B and the holder 33 by forming the connector 35B.

Herein, in a state where the treatment target is undergoing dissection by the heat generated in the heater 32, the temperature of the heater 32 and its vicinity is around 300° C. For this reason, if the temperature of the heater 32 and its vicinity is around 300° C. or lower than 300° C., the heater 32 works properly. However, if the temperature of the heater 32 and its vicinity rises to around 350° C., the influence of the heat on the heater 32 becomes significant, and the heater 32 may not work properly.

To this end, the temperature of the heater 32 and its vicinity was measured and verification was conducted for the case of insert molding of the connectors 35A and 35B in a manner similar to the present embodiment. In the verification, the temperature of the heater 32 and its vicinity was measured for the case where the connectors 35A and 35B are formed by insert molding using PEEK as a material. The temperature of the dies 101 and 102 was set at 200° C., and either one of PEEK or LCP at 400° C. was injected. When the connectors 35A and 35B were formed by insert molding under this condition in a manner similar to the present embodiment, the temperature of the heater 32 and its vicinity was kept lower than 250° C. during the insert molding of the connectors 35A and 35B.

As described above, in each case of the verification, when the connectors 35A and 35B were formed in a manner similar to the present embodiment, the increase in the temperature of the heater 32 and its vicinity up to around 350° C. was prevented in the insert molding of the connectors 35A and 35B. Accordingly, it was proved that the heater 32 was influenced almost not at all by the heat from the injected thermoplastic resin at the time of manufacture.

As described above, in the present embodiment, the heated thermoplastic resin is injected into the region distant from the heater 32 in the width direction during the insert molding. Furthermore, between the injected resin and the heater 32 there is the coating 52 of the holder 33 having a low thermal conductivity, in addition to the electrically conductive plate 31. For this reason, the heat from the injected resin is transferred to the heater 32 mainly through the electrically conductive plate 31, but is not easily transferred to the heater 32 through the coating 52 of the holder 33. Thus, in the insert molding of the connectors 35A and 35B, in other words, at the time of manufacture, the influence of the heat of the injected thermoplastic resin onto the heater 32 can be reduced. Through the reduction of the thermal influence on the heater 32 at the time of manufacture, the heater 32 works properly when it is used after manufacturing, and the heat generated in the heater 32 is used to perform a treatment appropriately.

In the present embodiment, the resin that constitutes the connectors 35A and 35B and the coating 52 of the holder 33 also has a melting point higher than the temperature of the treating surface 41 when treatment energy is applied to the treatment target. Then, under the state in which a treatment target undergoes dissection using the heat generated by the heater 32, namely the state in which the treating surface 41 has the temperature of around 300° C., the connectors 35A and 35B and the coating 52 do not become softened to a deformable extent. For this reason, in a treatment, such as a dissection of a treatment target using heat generated by the heater 32, for example, the deformation of the connectors 35A and 35B and the holder 33 can be prevented. It is thereby possible to effectively prevent the electrically conductive plate 31 from being detached from the connectors 35A and 35B and the holder 33.

(Modifications of First Embodiment)

In a first modification of the first embodiment shown in FIGS. 5 and 6, a core (for example, 51) is not provided in the holder 33, and the entire holder 33 is made from a resin. In this case, a material of the holder 33 may be a resin having a same composition as a resin constituting the coating 52 in the first embodiment, for example. The holder 33 is formed by injection molding of a resin. In the present modification, the entire holder 33 may be made from ceramics, instead of such a resin. In either case, the holder 33 is made of a material having thermal resistance and electric insulation properties, and properties of low thermal conductivity (a low thermal conductivity rate). Furthermore, the holder 33 has a lower thermal conductivity than that of the electrically conductive plate 31. In the present modification, the holder 33 supports the electrically conductive plate 31 from the back surface 46 side, and the heater 32 is arranged between the electrically conductive plate 31 and the holder 33.

In the present modification, a base 70 is provided in the jaw 16, and the base 70 supports the holder 33 from the side on which the jaw 16 opens. The base 70 continuously extends from the proximal portion to the distal portion of the jaw 16 in the direction along the longitudinal axis C' (the longitudinal direction of the end effector 8). The base 70 includes a core member 71 made of a metal, etc., and a coating 72 that coats the core member 71. Each of the core member 71 and the coating 72 continuously extends from the proximal portion to the distal portion of the jaw 16 (base 70) in the direction along the longitudinal axis C'. In the present modification, the core member 71 is abutted to the holder 33 from the side on which the jaw 16 opens. The coating 72 is formed at portions on both sides of the holder 33 in the width direction of the jaw 16, portions on both sides of the core member 71 in the width direction of the jaw 16, and a portion on the side on which the jaw 16 opens with respect to the core member 71.

In the present modification, a part of the coating 72 constitutes the connectors 35A and 35B, and the holder 33 is arranged between the connectors 35A and 35B in the width direction. Even in the present modification, the connector is provided on the opposite side of the connector 35B with respect to the longitudinal axis C' in the width direction. Each of the connectors 35A and 35B is arranged at a distance from the heater 32 toward an outer side in the width direction of the end effector 8, and is stationarily fixed to the holder 33. Furthermore, each of the connectors 35A and 35B stationarily fixes a corresponding one of the ends of the electrically conductive plate 31 in the width direction to the holder 33. Even in the present embodiment, an interface X1 is formed between the connector 35A and the holder 33, and an interface X2 is formed between the connector 35B and the holder 33.

The coating 72 is formed by insert molding (injection molding) wherein a resin is inserted to encapsulate the core member 71 and the holder 33, for example. As a material constituting the coating 72 including the connectors 35A and 35B, a thermoplastic resin having the same composition as the thermoplastic resin constituting the connectors 35A and 35B in the first embodiment is used for example, and it may be LCP or PEEK, etc. The coating 72 including the connectors 35A and 35B is made of a material having thermal resistance, electric insulation properties, and low thermal conductivity (a low thermal conductivity). Furthermore, the coating 72 has a lower thermal conductivity than that of the electrically conductive plate 31. The thermoplastic resin constituting the coating 72 (the connectors 35A and 35B) has a melting point higher than a temperature of the treating surface 41 when treatment energy, such as the heat generated at the heater 32 or a high-frequency current, is applied to the treatment target.

FIG. 6 shows the process of forming the connectors 35A and 35B in the present modification. As shown in FIG. 6, even in the present modification, the connectors 35A and 35B are formed using a pair of dies 101 and 102. In the present modification, the die 102 is a fixed type, and the die 101 is a movable type. When the connectors 35A and 35B are formed, the electrically conductive plate 31, the heater 32, the holder 33, and the core member 71 are stationarily fixed to the die 102, with the dies 101 and 102 being open to each other. At this time, with the electrically conductive plate 31 being supported by the holder 33 from the back surface 46 side, and with the core member 71 supporting the holder 33 from the side on which the jaw 16 opens, the electrically conductive plate 31, the heater 32, the holder 33, and the core member 71 are arranged.

Then, the dies 101 and 102 are closed to each other, and the electrically conductive plate 31, the heater 32, the holder 33, and the core member 71 are arranged in the cavity 103 thereby formed. At this time, in the cavity 103, a space is formed in the areas on both sides of the holder 33 and the core member 71 in the width direction of the jaw 16, and in the area on the side on which the jaw 16 opens with respect to the core member 71. In the space formed in the cavity 103, the engagement claw 61A is arranged on one side relative to the holder 33 in the width direction, and the engagement claw 61B is arranged on the other side relative to the holder 33 in the width direction. In the cavity 103, a heated and softened thermoplastic resin is injected into the space. At this time, the thermoplastic resin is injected into a region distant from the heater 32 according to the width direction. Then, the injected thermoplastic resin is cooled and hardened. Thus, the coating 72 is formed, and the thermoplastic resin forms into the connectors 35A and 35B on both sides of the holder 33 in the width direction. In other words, the connectors 35A and 35B are formed using the thermoplastic resin by insert molding at a region distant from the heater 32 in the width direction.

In the present modification, the heated thermoplastic resin is injected into the region distant from the heater 32 in the width direction during the insert molding. Furthermore, in addition to the electrically conductive plate 31, there is the holder 33 having low thermal conductivity between the injected resin and the heater 32. For this reason, the heat from the injected resin is transferred to the heater 32 mainly through the electrically conductive plate 31, but is not easily transferred to the heater 32 through the holder 33. Thus, in the present modification, similarly to the first embodiment, in the insert molding of the connectors 35A and 35B, in other words, at the time of manufacture, the influence of the heat of the injected thermoplastic resin onto the heater 32 can be reduced.

In a second modification of the first embodiment shown in FIG. 7, similarly to the first modification, the base 70 is provided, and the coating 72 of the base 70 constitutes the connectors 35A and 35B. In the present modification, a space 75 is formed between the holder 33 and the core member 71 of the base 70. Since the space 75 is formed, transfer of the heat of the heater 32 and the Joule heat caused by a high-frequency current to the back surface 42 of the jaw 16 becomes more difficult.

In a third modification of the first embodiment shown in FIGS. 8 and 9, instead of forming the anchor shape (63A and 63B) in the engagement claws 61A and 61B, through-holes 76A and 76B are formed in the engagement claws 61A and 61B, respectively. Each of the through-holes 76A and 76B passes through the corresponding engagement claw (either one of 61A and 61B) in the width direction of the jaw 16. Each of the through-holes 76A and 76B may extend continuously from the proximal portion to the distal portion of the jaw 16, in the direction along the longitudinal axis C', or may be formed discontinuously in the direction along the longitudinal axis C'. In the present modification, a filling (either 77A or 77B) to be filled into a corresponding through-hole (either one of 76A or 76B) is formed in each of the connectors 35A and 35B.

In the present modification, in the insert molding of the connectors 35A and 35B, the injected thermoplastic resin is filled into the through-holes 76A and 76B. Fillings 77A and 77B are thereby formed in the connectors 35A and 35B, respectively. In the present modification, a coupling strength between the engagement claw 61A or 61B and its corresponding connector (either 35A or 35B) can be improved by the through-holes 76A and 76B and the fillings 77A and 77B. The electrically conductive plate 31 is thereby firmly coupled to the holder 33.

Figure 11:
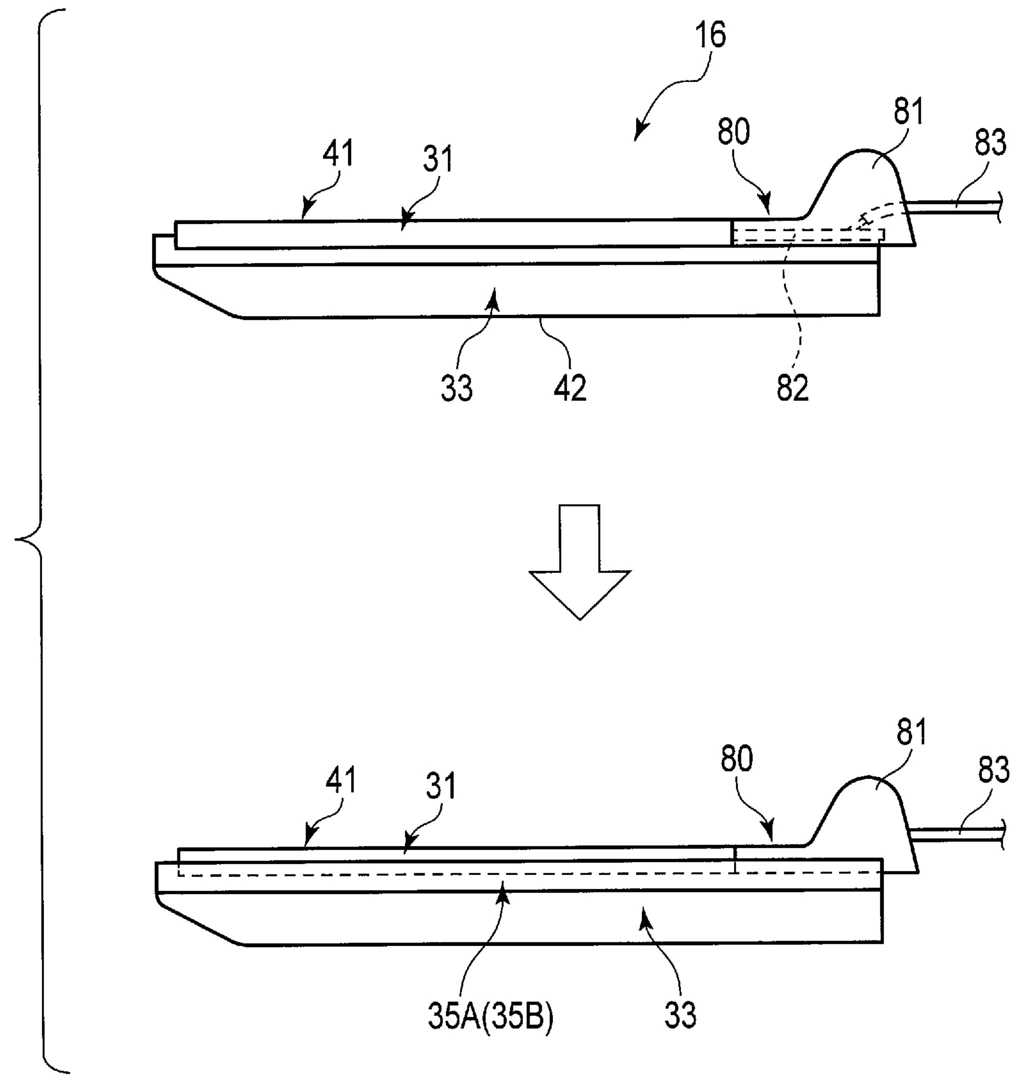
FIG. 11 is a schematic diagram explaining a process of attaching an electrically conductive plate and a block to a holder in manufacturing of either jaw in the fourth modification of the first embodiment.

In a fourth modification of the first embodiment shown in FIGS. 10 and 11, a block 80 is provided in the proximal portion of the jaw 16, and the block 80 is connected to the proximal side of the electrically conductive plate 31. The block 80 has electric insulation properties and is made of a material having properties of low thermal conductivity (a low thermal conductivity rate), such as a resin. In the block 80, the surface facing the side on which the jaw 16 closes is formed in parallel or substantially parallel to the width direction of the end effector 8. In the block 80, the projecting portion 81 projecting toward the side on which the jaw 16 closes is formed.

In the jaw 16, a circuit system 82 including a heater line of the heater 32 is provided. In the inside of the shaft 6, electric wiring 83 for supplying electric energy to the heater 32 extends. In the proximal portion of the jaw 16, a connecting portion of the circuit system 82 to the electric wiring 83 is formed. The block 80 serves as a cover that prevents exposure of the proximal portion of the circuit system 82 and the connecting portion of the electric wiring 83 to the circuit system 82. In a state in which a treatment target is grasped between the jaws 15 and 16, the projecting portion 81 of the block 80 prevents the invasion of the treatment target into the proximal side from the projecting portion 81. It is thereby possible to effectively prevent the invasion of the grasped treatment target into the inside of the shaft 6.

In the present modification, the holder 33 supports the electrically conductive plate 31 and the block 80 from the back surface 46 side of the electrically conductive plate 31. Furthermore, each of the connectors 35A and 35B stationarily fixes a corresponding one of the ends of the electrically conductive plate 31 in the width direction to the holder 33, and a corresponding one of the ends of the block 80 in the width direction to the holder 33.

In the present modification, in the insert molding of the connectors 35A and 35B, the thermoplastic resin is injected under a state in which the holder 33 supports the electrically conductive plate 31 and the block 80. Then, the injected resin is formed into the connectors 35A and 35B, and the electrically conductive plate 31 and the block 80 are attached to the holder 33 via the connectors 35A and 35B.

Figure 12:
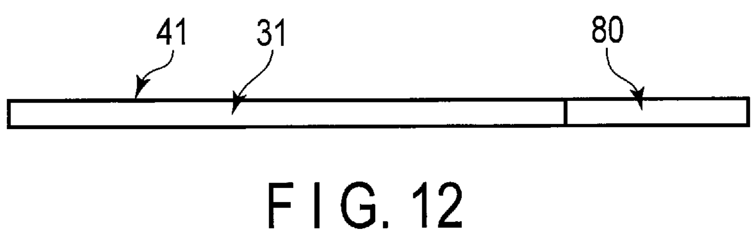
FIG. 12 is a schematic diagram showing an electric conductive plate and a block provided on either jaw according to a fifth modification of the first embodiment.

As in the fifth modification of the first embodiment shown in FIG. 12, a projecting portion (for example, 81) is not necessarily provided in the block 80. Even in this case, the block 80 prevents exposure of the proximal portion of the circuit system 82 and the connecting portion of the electric wiring 83 to the circuit system 82.

Second Embodiment

Next, the second embodiment will be explained with reference to FIGS. 13 and 14. The second embodiment is a modification of the processing in the first embodiment, as will be described below. Herein, the same elements as those in the first embodiment are specified by the same reference numbers, and a duplicate description of such elements will be omitted.

Figure 13:
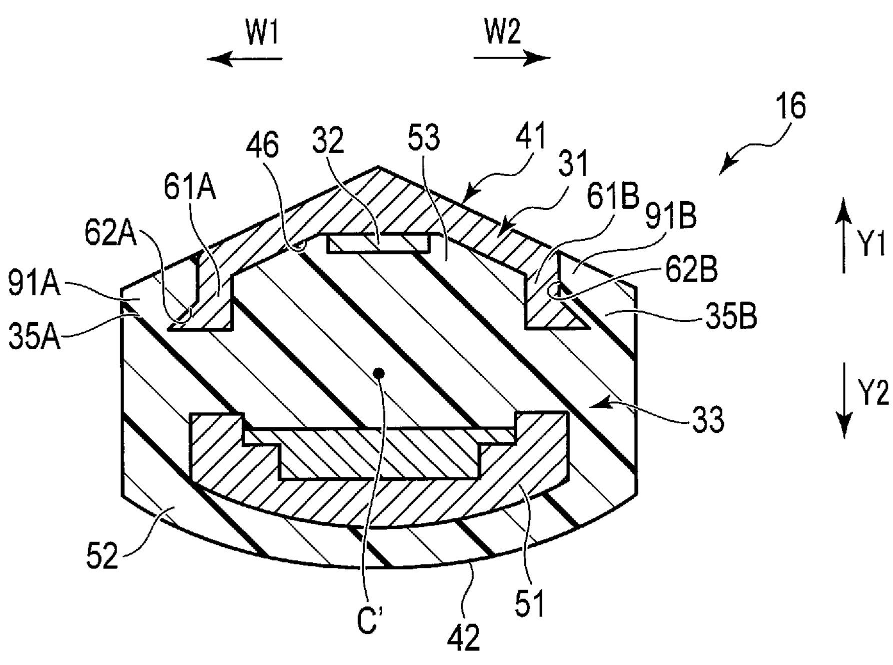
FIG. 13 is a cross-sectional view schematically showing either jaw according to a second embodiment in a cross section perpendicular or substantially perpendicular to a longitudinal direction.

As shown in FIG. 13, in the present embodiment, a part of the coating 52 of the holder 33 constitutes the connectors 35A and 35B. Also in the present embodiment, the connector 35A is provided on the opposite side of the connector 35B with respect to the longitudinal axis C' in the width direction. Each of the connectors 35A and 35B is arranged at a distance from the heater 32 in the width direction of the end effector 8. Furthermore, each of the connectors 35A and 35B stationarily fixes a corresponding one of the ends of the electrically conductive plate 31 in the width direction to the holder 33. In the present embodiment, however, the interfaces X1 and X2 are not formed because the connectors 35A and 35B are integrated with the holder 33.

Similarly to the first embodiment, the coating 52 of the present embodiment is also formed by insert molding (injection molding) of a resin into the core member 51. As a material constituting the coating 52 including the connectors 35A and 35B, a thermoplastic resin having the same composition as the thermoplastic resin constituting the connectors 35A and 35B in the first embodiment is used for example, and it may be LCP or PEEK, etc. Similarly to the first embodiment, the coating 52 including the connectors 35A and 35B of the present embodiment is also made of a material having thermal resistance and electric insulation properties, and properties of low thermal conductivity (a low thermal conductivity rate). Furthermore, the coating 52 has a lower thermal conductivity than that of the electrically conductive plate 31. The thermoplastic resin constituting the coating 52 (the connectors 35A and 35B) has a melting point higher than a temperature of the treating surface 41 when treatment energy, such as the heat generated at the heater 32 or a high-frequency current, is applied to the treatment target.

Similarly to the first embodiment, the coating 52 of the present embodiment includes the supporting projection 53 projecting toward the side on which the jaw 16 closes. In the present embodiment, in addition to the supporting projection 53, the coating 52 includes projections 91A and 91B projecting toward the side on which the jaw 16 closes. The projection 91A is arranged on one side relative to the supporting projection 53 in the width direction of the jaw 16, and the projection 91B is arranged on the other side relative to the supporting projection 53 in the width direction of the jaw 16. Each of the projections 91A and 91B is continuously formed from the proximal portion toward the distal portion of the jaw 16. Each of the projections 91A and 91B is arranged at a distance from the heater 32 according to the width direction of the end effector 8.

In the present embodiment, the engagement groove 62A is formed between the supporting projection 53 and the projection 91A in the width direction of the jaw 16. Then, the engagement claw 61A of the electrically conductive plate 31 engages the engagement groove 62A. Thus, in the coating 52, the engagement groove 62A and its vicinity constitute the connector 35A. Similarly, in the present embodiment, the engagement groove 62B is formed between the supporting projection 53 and the projection 91B in the width direction of the jaw 16. Then, the engagement claw 61B of the electrically conductive plate 31 engages the engagement groove 62B. Thus, in the coating 52, the engagement groove 62B and its vicinity constitute the connector 35B.

FIG. 14 shows the process of forming the connectors 35A and 35B in the present embodiment. In the present embodiment, similarly to the first embodiment, the coating 52 of the holder 33 is formed by the insert molding of the core member 51. However, as shown in FIG. 14, in the coating 52 formed by the insert molding, a concave portion 93A is formed between the supporting projection 53 and the projection 91A in the width direction. Similarly, in the coating 52 formed by the insert molding, the concave portion 93B is formed between the supporting projection 53 and the projection 91B in the width direction. At this time, each of the concave portions 93A and 93B continuously extends from the proximal portion to the distal portion of the holder 33.

Then, the electrically conductive plate 31 is supported by the holder 33 from the back surface 46 side. In one example, the engagement claws 61A and 61B of the electrically conductive plate 31 are moved along the longitudinal direction with respect to the holder 33, so as to be arranged at desirable positions. In another example, the engagement claws 61A and 61B of the electrically conductive plate 31 are arranged at desirable positions with respect to the holder 33 from the direction perpendicular to the longitudinal direction and the width direction. Thus, the supporting projection 53 of the holder 33 is abutted to the back surface 46 of the electrically conductive plate 31. Furthermore, the engagement claw 61A of the electrically conductive plate 31 is inserted into the concave portion 93A, and the engagement claw 61B of the electrically conductive plate 31 is inserted into the concave portion 93B. Herein, in the cross section perpendicular or substantially perpendicular to the longitudinal axis C' (the cross section intersecting with the longitudinal axis C'), the cross-sectional shape of each of the concave portions 93A and 93B is different from the cross-sectional shape of a corresponding one of the engagement claws 61A and 61B. For this reason, each of the engagement claws 61A and 61B can escape from the concave portion (either one of 93A or 93B).

In the present embodiment, the connectors 35A and 35B are formed using a heated horn 105. At this time, in a state in which the holder 33 supports the electrically conductive plate 31 and the engagement claws 61A and 61B are inserted into the concave portions 93A and 93B respectively, the heated horn 105 is brought into contact with the projections 91A and 91B of the coating 52. The heat is thereby supplied to the projections 91A and 91B of the coating 52. In other words, the heat is supplied to the coating 52 of the holder 33 at a region distant from the heater 32 in the width direction. Through the supply of the heat, the projections 91A and 91B made of the thermoplastic resin become softened and deformed. Then, the deformed projections 91A and 91B are cooled and hardened. Thus, the connectors 35A and 35B are formed on both sides of the holder 33 in the width direction. In other words, a part of the holder 33 (the projections 91A and 91B) is thermally caulked or swaged, thereby forming the connectors 35A and 35B in the holder 33.

Through the deformation of the projections 91A and 91B by the thermal caulking, the cross-sectional shape of each of the concave portions 93A and 93B in the cross section perpendicular to or substantially perpendicular to the longitudinal axis C' is deformed in the holder 33. The thermal caulking causes the change in the cross-sectional shape of each of the concave portions 93A and 93B, and in turn in the holder 33, and the change leads into the formation of the engagement groove 62A between the supporting projection 53 and the projection 91A in the width direction, and the formation of the engagement groove 62B between the supporting projection 53 and the projection 91B in the width direction. Through the formation of the engagement grooves 62A and 62B, the escape of the engagement claws 61A and 61B from respective engagement grooves 62A and 62B can be prevented.

Herein, the temperature of the heater 32 and its vicinity was measured and verification was conducted for the case of forming the connectors 35A and 35B by the thermal caulking in a manner similar to the present embodiment. In the verification, the temperature of the heater 32 and its vicinity was measured for the case where the coating 52 (the connectors 35A and 35B) of the holder 33 is made of PEEK. At this time, the temperature of the horn 105 was set to 350° C., and heat was supplied to the projections 91A and 91B of the holder 33. When the connectors 35A and 35B were formed under this condition in a manner similar to the present embodiment, the temperature of the heater 32 and its vicinity was kept lower than 300° C. during the thermal caulking of the projections 91A and 91B. In another verification, the temperature of the heater 32 and its vicinity was measured for the case where the coating 52 (the connectors 35A and 35B) of the holder 33 is made of LCP. At this time, the temperature of the horn 105 was set to 370° C., and heat was supplied to the projections 91A and 91B of the holder 33. When the connectors 35A and 35B were formed under this condition in a manner similar to the present embodiment, the temperature of the heater 32 and its vicinity was kept lower than 300° C. during the thermal caulking of the projections 91A and 91B.

As described above, in each case of the verification, when the connectors 35A and 35B are formed by thermal caulking in a manner similar to the present embodiment, the increase of the temperature of the heater 32 and its vicinity up to around 350° C. was prevented in the thermal caulking. Accordingly, it was proved that the heater 32 was influenced almost not at all by the heat supplied to the holder 33 at the time of manufacture.

As described above, in the present embodiment, the heat is supplied to the holder 33 in a region distant from the heater 32 according to the width direction when the connectors 35A and 35B are formed. Furthermore, in addition to the electrically conductive plate 31, there is the coating 52 of the holder 33 having a low thermal conductivity between the portion to which the heat is applied in the holder 33 and the heater 32. For this reason, the heat applied from the horn 105 is transferred to the heater 32 mainly through the electrically conductive plate 31, and is not easily transferred to the heater 32 through the coating 52 of the holder 33. Thus, in the formation of the connectors 35A and 35B, in other words, at the time of manufacture, the influence of the heat supplied to the holder 33 onto the heater 32 can be reduced. In other words, even in the present embodiment, similarly to the first embodiment, the thermal influence on the heater 32 at the time of manufacture can be reduced. Accordingly, also in the present embodiment, the heater 32 works properly when it is used after manufacturing, and the heat generated in the heater 32 is used to perform a treatment appropriately.

In the present embodiment, the resin that constitutes the coating 52 of the holder 33 including the connectors 35A and 35B also has a melting point higher than the temperature of the treating surface 41 when treatment energy is applied to the treatment target. Then, under the state in which a treatment target undergoes dissection using the heat generated by the heater 32, namely the state in which the treating surface 41 has a temperature of 300° C. or so, the coating 52 including the connectors 35A and 35B does not become softened to a deformable extent. For this reason, similarly to the first embodiment, the deformation of the connectors 35A and 35B and the holder 33 can be prevented in the present embodiment during a treatment, such as a dissection of a treatment target using heat generated by the heater 32, for example.

(Modifications of Second Embodiment)

Figure 15:
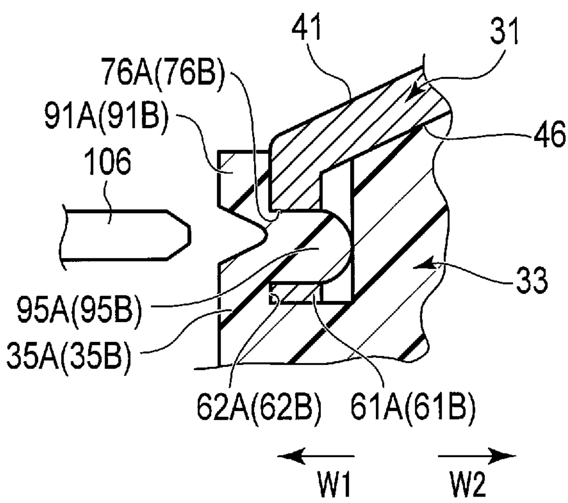
FIG. 15 is a cross-sectional view schematically showing a structure of a connector and its vicinity in either jaw according to a modification of the second embodiment.

In a modification of the second embodiment shown in FIG. 15, the through-holes 76A and 76B are respectively formed in the engagement claws 61A and 61B, similarly to the modification of the first embodiment shown in FIGS. 8 and 9. Even in the present modification, similarly to the second embodiment, the projections 91A and 91B are provided in the holder 33, as well as the connectors 35A and 35B in the holder 33. In the present modification, the inserted portions 95A and 95B, which are respectively inserted into the through-holes 76A and 76B, are respectively formed in the projections 91A and 91B. Each of the inserted portions 95A and 95B is inserted into a corresponding through-hole (either one of the through-holes 76A and 76B) from an outer side in the width direction of the jaw 16.

In the present modification, heat is supplied to the projections 91A and 91B of the holder 33 from a heated horn 106 so as to soften and deform the projections 91A and 91B, and the projections 91A and 91B are inserted into the through-holes 76A and 76B, respectively. In other words, the projections 91A and 91B are respectively inserted into the through-holes 76A and 76B by thermal caulking. Thus, the inserted portions 95A and 95B are respectively formed in the projections 91A and 91B of the holder 33. In the present modification, the through-holes 76A and 76B and the inserted portions 75A and 75B improve the coupling strength between the engagement claw 61A (61B) and the connector 35A (35B). The electrically conductive plate 31 is thereby more firmly coupled to the holder 33.

In another modification, the holder 33 is abutted only to the back surface 46 of the electrically conductive plate 31, and not to the heater 32. In this case, a space is formed between the holder 33 and the heater 32 in such a manner that the space is formed adjacently to the heater 32 on the side on which the jaw 16 opens.

In another modification, in a configuration wherein the connectors 35A and 35B are formed integrally with the holder 33, the block 80 is provided, similarly to the modification of the first embodiment shown in FIGS. 10 and 11. In this case, a part of the holder 33 is softened and deformed by thermal caulking, and the connectors 35A and 35B are thereby formed, and the electrically conductive plate 31 and the block 80 are attached to the holder 33 via the connectors 35A and 35B.

(Other Modifications)

In the foregoing embodiments, the heater 32 is provided as an electric component; however, in a modification, for example, a sensor that detects a temperature of the end effector 8 or a sensor that detects a position or a posture of the end effector 8 may be provided as an electric component. Also in this case, the sensor is electrically insulated from the electrically conductive plate 31 and electrically independent from the electrically conductive plate 31. In the present modification, electric energy is supplied to the electrically conductive plates 22 and 31 based on an operation at the operation apparatus 10. When electric energy is supplied to the electrically conductive plates 22 and 31, a high-frequency current flows between the electrically conductive plates 22 and 31 via the grasped treatment target, and the high-frequency current is thereby applied to the treatment target. At this time, the temperature of the treating surface 41 is between around 120° C. and 130° C. due to Joule heat caused by the high-frequency current. For this reason, in the present modification in which a sensor is provided instead of the heater 32 as an electric component, the connectors 35A and 35B are made of a thermoplastic resin that has a melting point higher than 130° C. and that does not get softened to a deformable extent at the temperature of 130° C. and the vicinity thereof.

In one modification, in a configuration with the electrically conductive plate 31 and electric components such as the heater 32 and the sensor, etc. electrically independent from the electrically conductive plate 31, similarly to the foregoing embodiments, a cutter that can move on the treating surface 41 of the electrically conductive plate 31 may be provided. In this case, the cutter is movable on the treating surface 41 along the longitudinal axis of the end effector 8. While a treatment target is being grasped between the jaws 15 and 16, the grasped treatment target undergoes dissection when the cutter is moved on the treating surface. In the foregoing embodiments, etc., the end effector 8 has a pair of jaws 15 and 16; however, in a modification, a counter electrode plate disposed in a subject (e.g., human body) is provided, instead of the jaw 15. In this case, electric energy is supplied to the electrically conductive plate 31 and the counter electrode plate based on an operation at the operation apparatus 10. Furthermore, when electric energy is supplied to the electrically conductive plate 31 and the counter electrode plate in a state in which the treating surface 41 of the electrically conductive plate 31 is in contact with the treatment target, a high-frequency current flows through the treatment target, and the high-frequency current is thereby supplied to the treatment target. In other words, the foregoing configuration is applicable not only to a treatment instrument that performs a bipolar treatment in which a high-frequency current flows between a pair of jaws, but also to a treatment instrument that performs monopolar treatment in which a high-frequency current flows between a counter electrode plate and an end effector.

Additional advantages and modifications will readily occur to those skilled in the art. Therefore, the exemplary embodiments in broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:

a plate extending along a longitudinal direction, the plate including:

a first surface; and a second surface, the second surface opposed to the first surface;

an electric component arranged on the second surface;

a holder supporting the electric component; and a connector connecting the holder and the plate, the connector being located between the plate and the holder in a thickness direction of the treatment instrument, the thickness direction being orthogonal to a planar portion of the second surface that contacts the electric component, wherein the electric component is surrounded by the holder and the plate.

2. The treatment instrument according to claim 1, wherein the holder includes:

a base; and a protrusion protruding from the base toward the plate.

3. The treatment instrument according to claim 2, wherein the protrusion includes a concave portion concaved from the second surface toward the base.

4. The treatment instrument according to claim 3, wherein the electric component is located in the concave portion, and the protrusion is in contact with the second surface.

5. The treatment instrument according to claim 1, wherein the connector includes:

a first connector arranged on a first end of the plate; and a second connector arranged on a second end of the plate, the second end of the plate opposed to the first end of the plate in a width direction, the width direction intersecting the longitudinal direction.

6. The treatment instrument according to claim 5, wherein the holder includes:

a base; and a protrusion protruding from the base toward the plate, wherein the protrusion is located between the first connector and the second connector.

7. The treatment instrument according to claim 1, wherein the connector is spaced apart from the electric component.

8. The treatment instrument according to claim 1, wherein the connector is made of a first resin.

9. The treatment instrument according to claim 8, wherein the holder is comprised a second resin, and the second resin includes the same material as the first resin.

10. The treatment instrument according to claim 1, wherein the electric component is a heater.

11. The treatment instrument according to claim 1, wherein the electric component is a sensor.

12. The treatment instrument according to claim 5, wherein the first connector and the second connector extend along the longitudinal direction.

13. The treatment instrument according to claim 5, wherein the first connector surrounds the first end of the plate, and the second connector surrounds the second end of the plate.

14. The treatment instrument according to claim 5, wherein the connector further includes:

a first groove engaging with the first end of the plate; and a second groove engaging with the second end of the plate.

15. The treatment instrument according to claim 2, wherein:

the plate has a first length in a width direction, the base has a second length in the width direction, the width direction intersects the longitudinal direction, and the first length is shorter than the second length.

16. The treatment instrument according to claim 2, wherein:

the plate has a first length in a width direction, the protrusion has a second length in the width direction, the width direction intersects the longitudinal direction, and the first length is longer than the second length.

17. The treatment instrument according to claim 2, wherein the plate is spaced apart from the base.

18. The treatment instrument according to claim 2, wherein:

the protrusion has a first length in a width direction, the base has a second length in the width direction, the width direction intersects the longitudinal direction, and the first length is shorter than the second length.

19. The treatment instrument according to claim 1, wherein the connector is not located outward in a width direction beyond an outermost surface of a widest portion of the holder in the width direction, the width direction intersecting the longitudinal direction.

20. The treatment instrument according to claim 1, wherein:

the connector includes:

a first connector connecting a first end of the plate and the holder; and a second connector connecting a second end of the plate and the holder, the second end of the plate being located on an opposite side of the first end of the plate, and the first connector is spaced apart from the second connector.

* * * * *